(12) United States Patent
Pan

(10) Patent No.: US 7,101,556 B2
(45) Date of Patent: Sep. 5, 2006

(54) PREPARATION AND USAGE OF PLASMODIUM FUSION ANTIGEN

(75) Inventor: Weiqing Pan, Shanghai (CN)

(73) Assignee: Second Military Medical University, Shanghai (CN)

( * ) Notice: Subject to any disclaimer, the term of this patent is extended or adjusted under 35 U.S.C. 154(b) by 0 days.

(21) Appl. No.: 10/467,198

(22) PCT Filed: Feb. 1, 2002

(86) PCT No.: PCT/CN02/00049

§ 371 (c)(1),
(2), (4) Date: Aug. 1, 2003

(87) PCT Pub. No.: WO02/072625

PCT Pub. Date: Sep. 19, 2002

(65) Prior Publication Data

US 2004/0063190 A1    Apr. 1, 2004

(30) Foreign Application Priority Data

Feb. 1, 2001    (CN) ............................... 01 1 05292

(51) Int. Cl.
| | |
|---|---|
| A61K 39/00 | (2006.01) |
| A61K 38/00 | (2006.01) |
| A61K 39/38 | (2006.01) |
| C12N 15/00 | (2006.01) |
| C12N 15/74 | (2006.01) |
| C07K 1/00 | (2006.01) |
| C07K 21/04 | (2006.01) |

(52) U.S. Cl. .............................. 424/194.1; 424/184.1; 424/185.1; 424/192.1; 424/193.1; 424/265.1; 424/268.1; 424/266.1; 424/272.1; 530/300; 530/350; 435/320.1; 435/252.1; 536/23.1; 536/23.6

(58) Field of Classification Search ................ 530/300, 530/350; 536/23.1, 23.6; 514/2, 44; 424/184.1, 424/185.1, 265.1, 268.1; 435/320.1, 252.1; 930/210

See application file for complete search history.

(56) References Cited

U.S. PATENT DOCUMENTS

| | | | |
|---|---|---|---|
| 4,643,896 A | | 2/1987 | Asakura et al. |
| 5,185,146 A | | 2/1993 | Altenburger |
| 5,229,110 A | | 7/1993 | DuBois et al. |
| 5,720,959 A | * | 2/1998 | Holder et al. ............. 424/272.1 |
| 5,766,597 A | * | 6/1998 | Paoletti et al. ............ 424/199.1 |
| 5,814,617 A | | 9/1998 | Hoffman et al. |
| 6,534,062 B1 | * | 3/2003 | Raz et al. ................. 424/193.1 |
| 6,551,586 B1 | * | 4/2003 | Davidson et al. .......... 424/93.2 |
| 6,593,463 B1 | * | 7/2003 | Chen et al. ................ 536/23.7 |
| 6,669,945 B1 | | 12/2003 | Nardin et al. |
| 6,855,322 B1 | * | 2/2005 | Lyon et al. ............... 424/268.1 |
| 6,933,130 B1 | * | 8/2005 | Bujard et al. .............. 435/69.1 |
| 2003/0032787 A1 | * | 2/2003 | Lanar et al. ............... 536/23.1 |
| 2004/0063190 A1 | * | 4/2004 | Pan .......................... 435/252.3 |
| 2004/0091971 A1 | * | 5/2004 | Kocken et al. ............ 435/69.3 |
| 2005/0208068 A1 | * | 9/2005 | Milich et al. ............. 424/189.1 |
| 2006/0018911 A1 | * | 1/2006 | Ault-Riche et al. ...... 424/178.1 |
| 2006/0018932 A1 | * | 1/2006 | Longacre-Andre et al. ...... 424/272.1 |

FOREIGN PATENT DOCUMENTS

| | | | |
|---|---|---|---|
| EP | 1357128 A1 | * | 10/2003 |
| WO | WO 95/21192 A | | 8/1995 |
| WO | WO 98/14583 A | | 4/1998 |
| WO | WO 00/63245 A | | 10/2000 |
| WO | WO 02/72625 A1 | * | 9/2002 |

OTHER PUBLICATIONS

Zhang et al, Shengwu Huaxue Yu Shengu Wuli Xuebao, 2003, 35/4:345-349 Abstract Only.*
Ming et al, Chinese medical Journal, Aug. 1999, 112/8:691-697 Abstract Only.*
Enders et al, Mem. Inst. Oswaldo Cruz, 1992, 87/Suppl. 3:413-422 Abstract Only.*
Sallberg et al, Intervirology, 2002, 45/4-6:350-361 Abstract Only.*
Burns et al, Vaccine, May 2003, 21/17-18:1843-1852 Abstract Only.*
Anders et al, Vaccine, 1998, 16/2-3:240-247 Abstract Only.*
Patarroyo et al, Nature, 1987, 328:629-632.*
Peterson et al, Molecular and Cellular Biology, 1989, 9/7:3151-3154.*
Stoute et al, New England J. Medicine, 1997, 336:86-91.*
Gardner et al, Nature, 2002, 419:498-511.*
Marshall et al, Molecular and Biochemical Parasitology, 1996, 11:109-113.*
Kester et al, J. Infectious Diseases, 2001, 183:640-647.*
Lalvani et al, J. Infectious Diseases, 1999, 180:1656-1664.*
Jones et al, Vaccine, 1999, 17:3065-3071.*
Bojang et al, lancet, 2001, 358:1927-1934.*
Garcon et al, Expert Rev. Vaccines, 2003, 2/2:231-238.*
Kim et al, Korean J. Parasitology, 2003, 41/4:203-207.*
Stowers et al, Infection and Immunity, 2001, 69/3:1536-1546.*

(Continued)

Primary Examiner—N. M. Minnifield
(74) Attorney, Agent, or Firm—Dorsey & Whitney, LLP

(57) ABSTRACT

The invention provides a fusion protein comprising the *Plasmodium* merozoite surface protein-1 (MSP1) and the *Plasmodium* apical membrane antigen 1 (AMA-1), the encoding DNA sequence, the vector containing the sequence, the host cell containing the vector, and the genetic engineering method for preparing the fusion protein and the usage for producing anti-malarial vaccine. The AMA-1/MSP1 fusion protein of the present invention has excellent immunogenicity and can cause an effective immune response against *Plasmodium* in individuals.

10 Claims, 8 Drawing Sheets

OTHER PUBLICATIONS

Daly et al, infection and Immunity, 1996, 64/7:2602-2608.*
Kang et al, J. Immunology, 1998, 161:4211-4219.*
Pan et al, Nucleic Acids Research, 1999, 27/4:1094-1103.*
Adda et al, Infection and Immunity, 1999, 67/9:4679-4688.*
Ahlborg et al, Infection and Immunity, 2002, 70/2:820-825.*
Fries et al, PNAS USA, 1992, 89:358-362.*
Kim et al, Yonsei Medical Journal, 2004, 45/1:129-134.*
Perraut et al, Infection and Immunity, 1995, 63/2:554-562.*
Ramasamy et al, BBA, 1999, 1453:1-13.*
Carucci, Vaccine, 2001, 19:2315-2318.*
Smooker et al, Vaccine, 2000, 18:2533-2540.*
Gilbert et al, Parasitology Today, 1997, 13/8:302-306.*
Nacher, TRENDS in Parasitology, 2001, 17/12:563-565.*
Butcher et al, Parasitology Today, 2000, 16/2:43-44.*
Taylor-Robinson, TRENDS in Microbiology, 1999, 7/1:15.*
Senoir, Molecular Medicine Today, Jan. 1999, pp. 2-3.*
Doolan et al, Parasitology Today, 1997, 13/5:171-178.*
Plebanski et al, Current Opinion in Immunology, 2000, 12:437-441.*
Jones et al, Vaccine, 2002, 20:1675-1680.*
Arevalo-Herrera et al, Molecular Immunology, 2001, 38:443-455.*
Uhlemann et al, Molecular and Biochemical Parasitology, 2001, 118:41-48.*
Stowers et al, TRENDS in Parasitology, 2001, 17/9:415-419.*
Heppner et al, TRENDS in Parasitology, 2001, 17/9:419-425.*
Anders et al, Parasitology Today, 2000, 16/10:444-447.*
Tatsis et al, Molecular Therapy, 2004, 10/4:616-629.*
Barnwell et al, Experimental Parasitology, 1999, 91:238-249.*
Hommel et al, Parasitology Today, 1998, 14/9:337-340.*
Galinski et al, Parasitology Today, 1996, 12/1:20-29.*
Herrera et al, International J. Parasitology, 2002, 32:1625-1635.*
Epstein et al, Vaccine, 2004, 22:1592-1603.*
Zhou et al, Protein Expression and Purification, 2004, 34:87-94.*
Rogers et al, Vaccine, 1999, 17:3136-3144.*
Shi et al, Vaccine, 2000, 18:2902-2914.*
Rafi-Janajreh et al, Experimental Parasitology, 2002, 101:3-12.*
Doolan et al, international J. parasitology, 2001, 31:753-762.*
Cox, Nature, 1992, 360:417-418.*
Kurtis et al, Infection and Immunity, 1999, 67/7:3424-3429.*
Joshi et al, Infection and Immunity, 2000, 68/1:141-150.*
Kurtis et al, TRENDS in Parasitology, 2001, 17/5:219-223.*
Shi et al, PNAS USA, 1999, 96:1615-1620.*
Ntumngia et al, Molecular and Biochemical Parasitology, 2004, 137:349-353.*
Ballou et al, Am. J. Trop. Med. Hyg., 2004, 71/Suppl. 2:239-247.*
Moorthy et al, Lancet, 2004, 363/9403:150-156 Abstract only.*
Wu et al, J. Biotechnology, 2000, 83:125-135.*
Pan et al, J. Immunology, 2004, 172:6167-6174.*
Healer et al, Infection and Immunity, Apr. 2005, 73/4:2444-2451.*
Pedro L. Alonso, et al., "Efficacy of the RTS,S/AS02A Vaccine Against Plasmodium Falciparum Infection and Disease in Young African Children: Randomised Controlled Trial", www.thelacncet.com, vol. 364, Oct. 16, 2004, pp. 1411-1420.
W. Ripley Ballou et al., "Update on the Clinical Development of Candidate Malaria Vaccines", Am. J. Trop. Med. Hyg., 71(Suppl 2), 2004, pp. 239-247.
Sandra P. Chang, et al., "A Recombinant Baculovirus 42-Kilodalton C-Terminal Fragment of Plasmodium Falciparum Merozoite Surface Protein 1 Protects Aotus Monkeys against Malaria", Infection and Immunity, vol. 64, No. 1, Jan. 1996, pp. 253-261.
George S. N. Hui, et al., "Research Brief: Serum from Pf195 Protected Aotus Monkeys Inhibit Plasmodium Falciparum Growth in Vitro", Experimental Parasitology, 64, 519-522 (1987).

* cited by examiner

A: PfCP-1

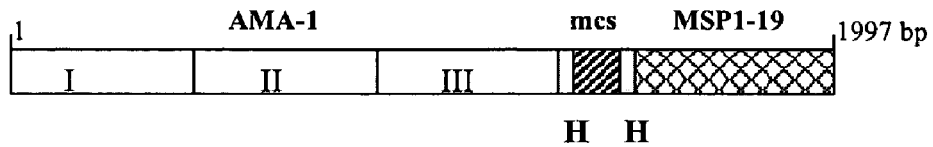

PfCP-1 N-terminus:
```
    XhoI
    CTC GAG AAA AGA CAG AAT TAC TGG ---------
    Leu Glu lys arg Gln Asn Tyr Trp ---------
```

PfCP-1 C-terminus:

PfCP-1$^{-his}$
```
--------- TCC TCT AAT TAA TAG GAA TTC
--------- Ser Ser Asn Stop codon EcoRI
```
PfCP-1$^{+his}$
```
--------- TCC TCT AAT CAC CAT CAC CAT CAC CAT TAA TAG GAA TTC
--------- Ser Ser Asn His His His His His His Stop codon EcoRI
```

B: PfCP-2

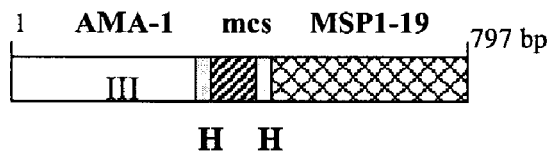

PfCP-2 N-terminus:
```
    XhoI
    CTC GAG AAA AGA CAA CAA TCA TCT TAC ATT ---------
    Leu Glu lys Arg Gln Gln Ser Ser Tyr Ile ---------
```

PfCP-2 C-terminus: same as that of PfCP-1

Fig. 1

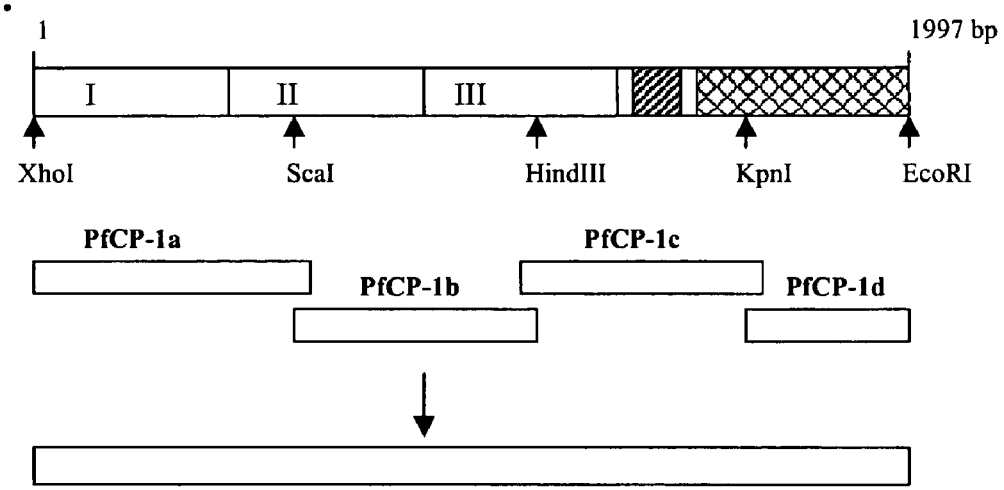
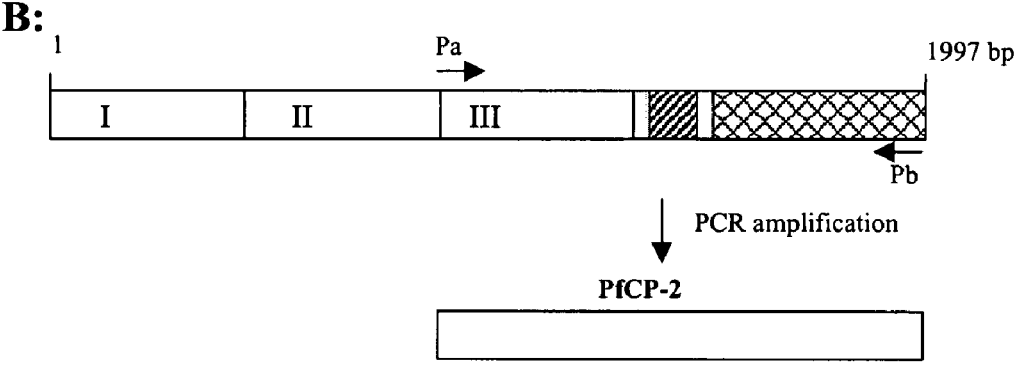
Fig. 2
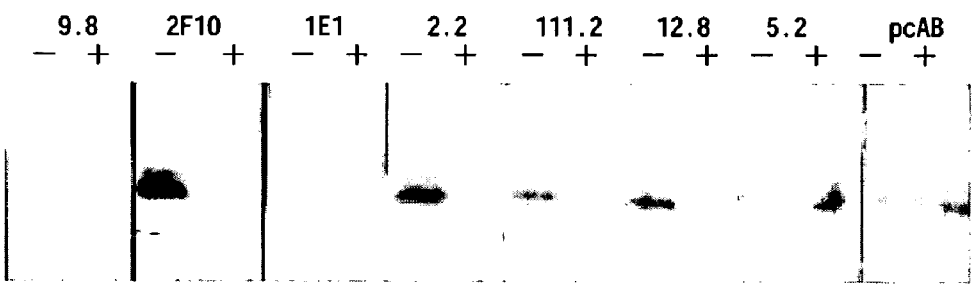
Fig. 8

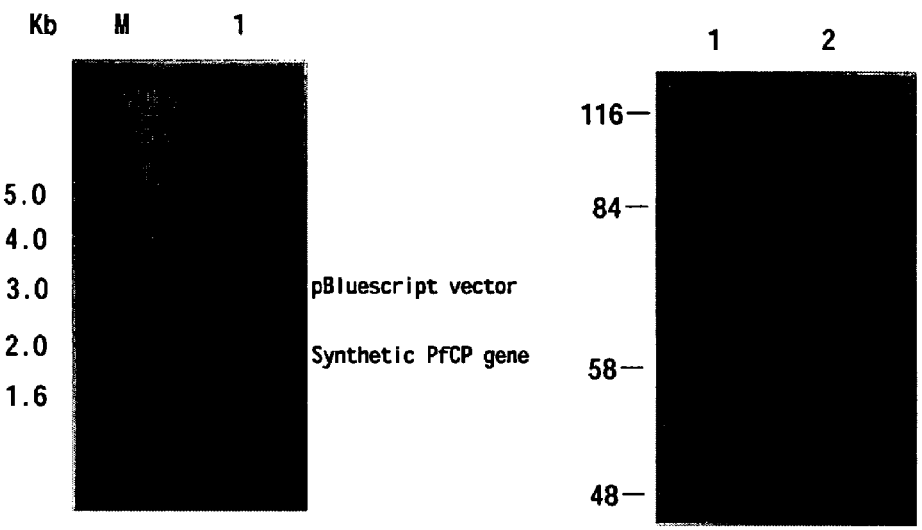
Fig. 3
Fig. 6
Fig. 7
Fig. 9

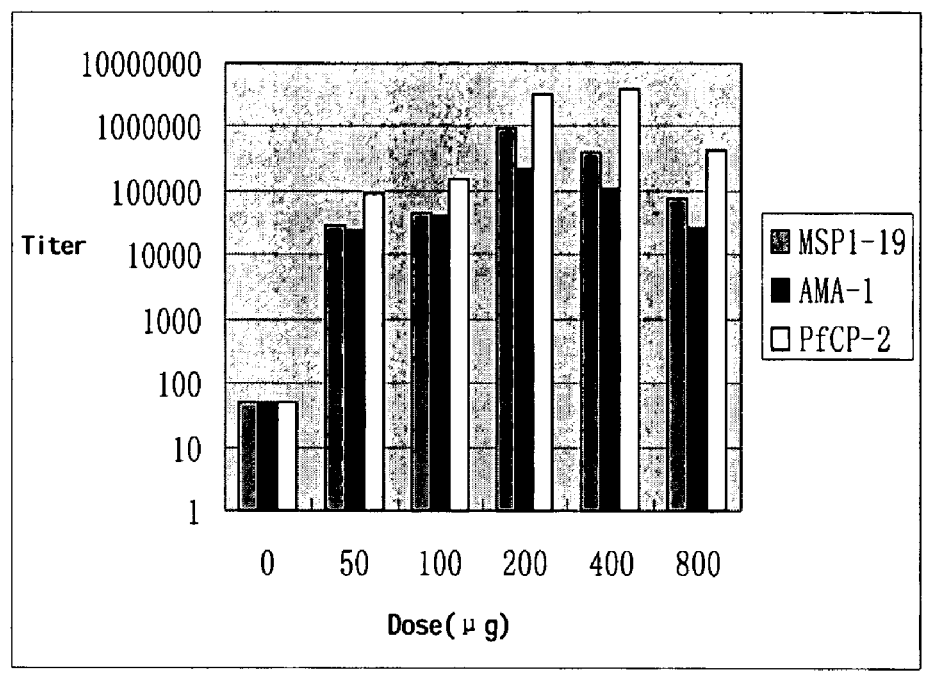
图 12
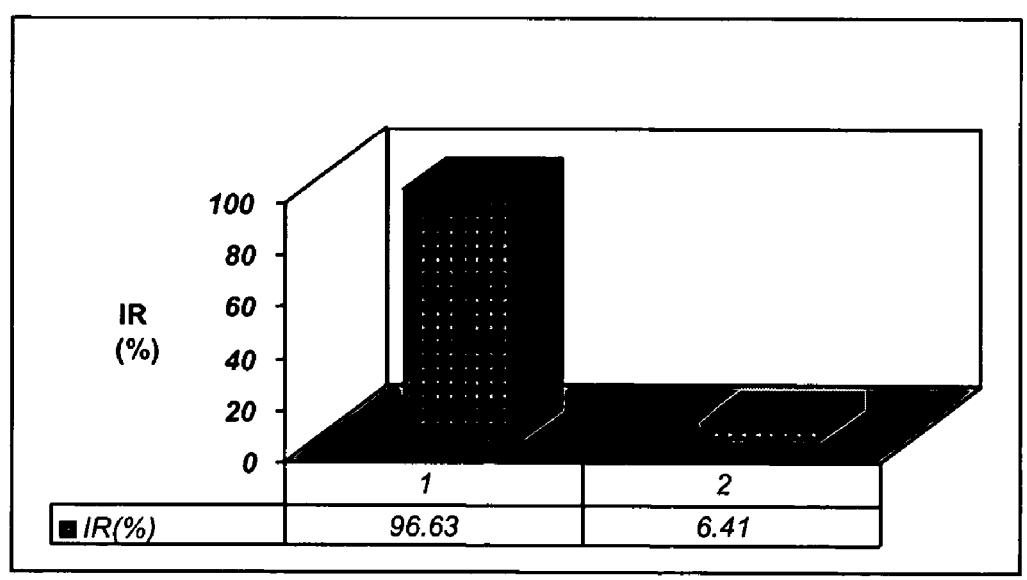
Fig. 13

PREPARATION AND USAGE OF PLASMODIUM FUSION ANTIGEN

FIELD OF INVENTION

The present invention relates to DNA recombinant techniques and gene engineering vaccines. More specifically, the present invention relates to a fusion protein containing Merozoite Surface Protein 1 (MSP1) and Apical Membrane Antigen-1 (AMA-1) of *Plasmodium*, a DNA sequence encoding the fusion protein, a vector containing the DNA sequence, host cells containing the vector, a genetic engineering method to prepare the fusion protein, and uses of the fusion protein in developing vaccine against malaria.

BACKGROUND

Malaria is one of the most ancient infectious diseases that still has strong impact upon human health. According to the World Health Organization (WHO), about 40% of the world's population are still under the threat of malaria, which has been distributed to more than 100 countries. Today, there are about 300–500 million malaria cases every year, of which about 3 million die from it. Moreover, because of the emergence and quick spread diffusion of drug resistance by plasmodia and mosquito vector, malaria has not been effectively controlled. On the contrary, it is likely to stage a comeback. Thus the expansion of a global project to control malaria has become one of the emphatic study fields of WHO in the new century.

People can depend upon or expect to achieve breakthrough in controlling malaria through three main pathways: anti-malaria drugs, malaria vaccines and mosquito vector control. However, anti-malaria drugs and mosquito vector control are facing great difficulties and challenges, which have been the result of the emergence and spread of drug resistance of plasmodia and mosquito. Although the malaria vaccine with application value has not become visible at present, it is still generally believed that the development of malaria vaccine is an important pathway for human beings to control and even eradicate malaria.

Many studies have indicated that the prevention of malaria could be achieved through the development of effective vaccines. For example, volunteers immunized by inactivated sporozoit could be completely protected against subsequent challenge of *Plasmodium falciparum*. Also, the mouse immunized by murine *Plasmodium* recombinant antigen could be completely protected against subsequent infection attacks from homogenous *Plasmodium*. In addition, epidemiological studies on malaria also demonstrates that the population dying from malaria is mainly those having no immunity against malaria, e.g. children living in malaria endemic areas and population from malaria non-endemic areas entering malaria endemic areas, while adults in malaria endemic areas seldom die of it. If inoculating these people having no specific immunity with effective vaccines, it could be expected that the specific immunity could be induced similar to that of the adults from malaria endemic areas, and thus the objective to prevent malaria and reduce malaria mortality can be achieved. Hence, the development of malaria vaccines has become the hot topic in the world nowadays.

In the development of malaria vaccines, the studies upon two candidate vaccines have ever been widely noticed, and one of which is anti-sporozoit vaccine. This vaccine could induce immunity to inhibit invasion of sporozoit into hepatic cells. However, subsequent clinical trials do not show good efficacy. According to the analysis, the vaccine could just generate immunity against sporozoit, but even if only a few sporozoit escapes the immune attack of the vaccine and survive, they could invade hepatic cells and develop and proliferate to generate thousands of merozoites enough to cause disease in hosts. The other one is SPf66 polyvalence synthetic peptide vaccine. This vaccine is a 45-peptide polymer made of three 10-peptide epitopes separately linked through hydrophobic amino acids (Patarroyo, M. E., et al., Induction of protective immunity against experimental infection with malaria Suing Synthetic peptides, Nature; 328: 629, 1987). This vaccine achieved good immune protection against challenge of *Plasmodium falciparum* in Aotus monkeys. However, an ideal clinical protection has not been achieved in the subsequent clinical trials in Africa, South-east Asia and Latin America, and thus no applicable value was established. The reason of failure of this vaccine may lie in the fact that SPf 66 only has 45 peptides. In such a short, chained peptide sequence, there may not be T cell epitopes enough for most individual MHC molecules to bind, which results in the prevention of antigen presentation.

Although the studies on malaria vaccines using biotechnology have been conducted for about 20 years, a vaccine with application value has yet to become available. It can be seen that the breakthrough in malaria vaccines still calls for further confirmation on the candidate antigens providing protection against malaria, clarification on the immunological mechanism of protection effect, and establishment of new strategies about malaria vaccine development.

Thus, it is urgently required in the art to develop effective immunogens and related vaccines against malaria.

SUMMARY OF INVENTION

The purpose of the present invention is to provide a fusion protein produced by genetic engineering technique. The fusion protein can trigger immune response as an effective immunogen against malaria, and thus enable the immunized individual to obtain immunity against malaria.

Another purpose of the present invention is to provide a new immunogen that could be used in malaria vaccines. Said immunogen is a fusion protein that contains AMA-1 and MSP1 antigens ("AMA-1/MSP1 fusion protein"), and also to provide a vaccine composition comprising the immunogen.

Another purpose of the present invention is to provide a DNA encoding the fusion protein, a vector containing the DNA sequence, and host cells containing the vector.

Another purpose of the present invention is to provide a low-cost and/or simple method for producing the AMA-1/MSP1 fusion protein.

The first aspect of the present invention is to provide a fusion protein, which comprises the amino acid sequence of *Plasmodium* apical membrane antigen-1, the amino acid sequence of *Plasmodium* merozoite surface protein 1, and a hinge between the amino acid sequence of the apical membrane antigen-1 and the amino acid sequence of the merozoite surface protein 1.

More preferably; the fusion protein comprises the amino acid sequence shown in SEQ ID NO: 1, 2 or 3.

The second aspect of the present invention is to provide an isolated DNA molecule, which encodes the above fusion protein of the present invention.

The third aspect of the present invention is to provide a vector, which contains the DNA molecule described above, and a host cell containing the vector.

The fourth aspect of the present invention is to provide a method for producing the fusion protein of the present invention, which comprises the following steps:

growing the host cells described above under conditions appropriate for the expression of the fusion protein, thereby expressing the fusion protein; and isolating the fusion protein.

The fifth aspect of the present invention is to provide a vaccine, which contains the fusion protein or the encoding DNA molecule described in the present invention.

The sixth aspect of the present invention is to provide an antibody, which specifically binds to the fusion protein of the present invention.

The seventh aspect of the present invention is to provide a method for constructing an anti-malaria multivalent vaccine, which comprises the steps of fusing several conformational Plasmodium antigens or functional domains into a fusion protein molecule. In particular, the method comprises the following steps: (1) fusing several Plasmodium antigens or the functional domain thereof (especially the antigen or functional domain with conformation) into a fusion protein molecule (in which a hinge is inserted between adjacent antigens or functional domains), and thereby obtain its amino acid sequence; (2) according to the amino sequence, designing its nucleotide encoding sequence; (3) synthesizing the nucleotide encoding sequence (and optionally modifying the encoding sequence according to codon preference, etc.); (4) introducing the nucleotide encoding sequence into host cells to obtain the transformed host cells; (5) incubating the transformed host cells under proper conditions to express the fusion protein; (6) isolating or purifying the fusion protein to use as an anti-malaria multivalent vaccine.

DESCRIPTION OF DRAWINGS

FIG. 1: Schematic diagrams of PfCP-1 (FIG. 1A) and PfCP-2 (FIG. 1B) fusion protein and the N and C terminal sequences thereof. Ectodomain of AMA-1 was suggested to be divided into three regions, namely regions I, II and III. MSP1-19 is the 19KD C terminal region of MSP1. MCS is a multiple cloning site region that contains 8 single restriction cleavage sites, which is used for further insertion of other antigen genes. H is a hinge sequence, which is made of repeated sequences of Gly-Pro-Gly, and is used to prevent the two proteins from interacting in conformation with each other.

FIG. 2 is the synthetic strategy schematic diagram for the fusion antigen gene PfCP-1 (FIG. 2A) and PfCP-2 (FIG. 2B).

FIG. 2A: Synthesis of PfCP-1 gene: 1997 bp PfCP-1 gene is divided into 4 segments and each of the segments is synthesized separately. The name and length of these 4 segments are: PfCP-1a, 512 bp; PfCP-1b, 629 bp; PfCP-1c, 575 bp; PfCP-1d, 395 bp respectively. XhoI and EcoRI sites are added to the 5' and 3' end of each segment for gene segment cloning. Each synthesized segment is first cloned into a pBluscript vector and then undergoes sequence analysis. Each segment is linked to generate the full-length PfCP-1 gene through ScaI, HindIII and KpnI sites shown in the figure.

FIG. 2B: Synthesis of PfCP-2 gene: a pair of primers are designed respectively at the start point (Pa) of PfCP-1 AMA-1 (III) and the 3' terminal (Pb), which is obtained through amplification with PCR method.

FIG. 3: Agarose gel electrophoresis showing the full-length PfCP-1 gene. After cutting with XhoI and EcoRI enzyme, electrophoresis shows the PfCP-1 synthesized gene and the vector bands (lane 1).

FIG. 6: Western blot detection of PfCP-1 expression, in which lane 2 is the supernatant from the culture before induction, and lane 1 is the supernatant from the culture at 72 hours after induction. The monoclonal antibody mAb5.2 which recognizes the conformation epitopes of MSP1-19 and the secondary antibody anti-mouse IgG are used for detection.

FIG. 7: the detection of PfCP-2 expression by SDS-PAGE. 10 ul of culture supernatant is loaded on the SDS-PAGE gel and Coomassie-stained at 0 hr before induction and 24, 48, 72 and 96 hr after induction. The doublet of the products are presented at the 32KD location. N-terminal amino acid sequence analysis of the doublet shows that 9 amino acid residues are deleted at the N-terminal of the lower band.

FIG. 8: the reaction of a monoclonal antibodies with PfCP-2. The mAbs ZF10, IE1, 2.2, 111.2, 12.8 and 5.2 are all specific monoclonal antibodies used to identify conformation epitopes. The mAb 9.8 is the negative control, and PCAB is anti-AMA-1 polyclonal antibody. "−" means that β-mercapto-ethanol was not present in the sample; "+" means that β-mercaptoethanol was added in the sample. The illustration involves the procedures of applying equal amount of PfCP-2 expression supernatant to each lane, performing electrophoresis and transferring to the membrane, and using the above antibodies and the corresponding secondary antibody to proceed with reaction and staining.

FIG. 9: the SDS-PAGE gel showing the purified PfCP-2 recombinant protein. The expression product was purified from the supernatant in two steps with Ni column and gel filtration chromatography. According to SDS-PAGE and HPLC measurement, the purity of the target protein is above 98%. Each lane respectively is: lane 1, 10 ug; lane 2, 20 ug; and lane 3, 30 ug.

FIG. 12: the anti-AMA-1 and MSP1 specific IgG level of the immunized rabbit serum measured by ELISA. AMA-1 expressed and refolded in E. coli and MSP1-19 expressed in yeast are respectively used as the antigens to measure each specific antibody, in which the horizontal scale is the different doses of the immune serum of the PfCP-2 antigen immunized rabbit; and the ordinate scale is the antibody titer measured by ELISA.

FIG. 13: the in vitro inhibition of the parasite growth by immune sera(1). Each group respectively is: 1. Freund's adjuvant+PfCP-2 (15% serum concentration), and 2. Freund's adjuvant.

DETAILED DESCRIPTION

Figure 4:
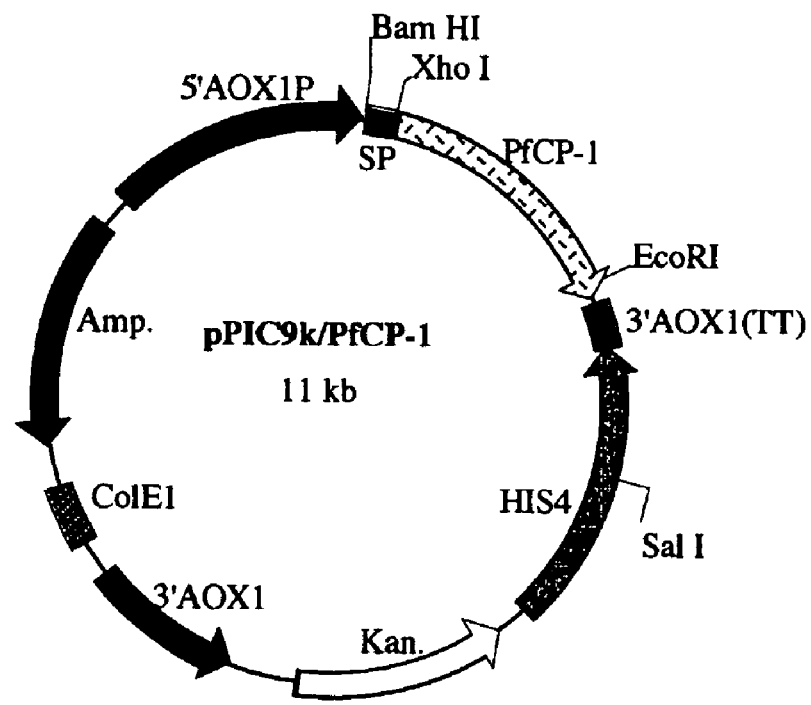
FIG. 4: the schematic diagram for the pPIC9k/PfCP-1 recombinant expression plasmid.

The studies have indicated that the life cycle of plasmodia is complicated, and the antigens stage-specific. Besides, there is severe antigen variation in *Plasmodium*. Based upon these characteristics, an effective and continuously applicable malaria vaccine should include quite a few *Plasmodium* protective antigens, from which the immunity generated should be capable of attacking different stages of the parasite. Thus, even if a few parasites could survive under the immune attack from the first defensive line for reasons such as antigen mutation, these parasites still will experience attacks from each subsequent defensive line, until all the parasites are eliminated. At present, more than 20 proteins have been considered as the candidate antigens for malaria vaccine. Seven of the candidate antigens were mixed to form a multivalent vaccine, and clinical trial was performed. Among 35 volunteers receiving vaccination, only 1 had obtained protection. As measured, the immunized individuals have very low antibody titer for each antigen. This may be caused by the antigen competition when various antigens injected simultaneously, and thus affect the immune response of the body to each antigen.

Another practical problem about malaria vaccines is human MHC polymorphism. Because of the polymorphism, some antigens can not bind to MHC molecules, and it leads to the inhibition of antigen presentation, and the non immune responses phenomenon in immunized individuals. To ensure that the vaccine would be effectively presented in most individuals, it is necessary to identify the multi-reaction epitopes from malaria antigens that could recognize MHC molecules in most population, and incorporating them into a vaccine, or incorporating various antigens to form a fusion antigen to overcome the problem with lack of enough T cell epitopes in unique antigen are required.

An effective malaria vaccine needs to incorporate multiple antigens, while the simple mixture of multiple antigens may cause the problem of antigen competition. Therefore, we developed another route to construct the multivalent vaccine antigen after wide and deep research, i.e. first identify the protective domains or regions from existing candidate antigens. These functional domains were then assembled to a fusion protein via appropriate design, and the gene of the protein was redesigned and synthesized. finally, the recombinant protein were expressed. Through the designing and insertion of a hinge sequence, the functional domains in this fusion protein could maintain their conformation. As a result, it is found that the fusion comprising merozoite surface protein 1 (MSP1) and apical membrane antigen-1 (AMA-1) of *Plasmodium falciparum* could effectively induce protective immune response. And the invention is accomplished upon this basis.

The fusion protein of the present invention involves two antigens of *Plasmodium falciparum*. One is merozoite surface protein 1 (MSP1) and the other is apical membrane antigen-1 (AMA-1). Both of them are important candidate antigens for malaria vaccines at present. The Aotus monkeys immunized with the MSP1 extracted from cultured *Plasmodium falciparum* could be completely protected against challenge of homologous strain *Plasmodium falciparum* (Siddqui, W. A. et al., Merozoite surface coat precursor protein completely protects Aotus monkeys against *Plasmodium falciparum* malaria. Proc. Natl. Acad. Sci. USA, 84: 3014, 1987). Many experimental evidences have indicated that MSP1 19 KD C-terminal segment (MSP1-19) is the functional domain for protective immunity of this antigen. Both MSP1-19 immune serum and monoclonal antibody could inhibit the in vitro growth of malaria parasite. This domain contains 10 cysteine residues, which form two Epidermal Growth Factor (EGF) like domains. The Aotus monkeys immunized with recombinant protein containing MSP1-19 could also be protected against subsequent challenge.

AMA-1 is a membrane protein with about 60 KD molecular weight. Immune serum against the ectodomain inhibited the in vitro growth of the parasite. The mouse immunized with an analogous of mouse *Plasmodium* AMA-1 could also be protected against challenge of the same species of the *Plasmodium*. AMA-1 contains 16 conserved cysteine residues, forming 3 domains linked by disulfide bonds, wherein domain III[AMA-1 (III)] is very conserved in sequence. It is presumed that the newly invading merozoite still carries this domain sequence, which may take part in the merozoite invasion.

The result of studies indicates that the protective effects of both AMA-1 and MSP1-19 are dependent upon the conformation formed by disulfide bonds in the antigens. Reduced and alkylated antigens failed to generate an effective immune protection effect. Hence, the key in fusing these two antigens into one molecule is to maintain the natural conformation of each antigen.

The present invention has constructed two fusion antigens AMA-1/MSP1-19 (named as PfCP-1) and AMA-1 (III)/MSP1-19 (named as PfCP-2), and expressed these antigens in yeast *Pichia pastoris*. The analysis shows that the protein resembled very close to the natural one. This antigen is highly immunogenic with ELISA titer at >4 million. The antibodies of the fusion antigen recognized the individual AMA-1 and MSP1 protein of the fusion protein. The immune serum against the fusion antigen completely inhibited the growth of the parasite in vitro after being diluted 6.7 times.

As used herein, the terms "the fusion protein of merozoite Apical Membrane Antigen-1 and Merozoite Surface Protein 1", and "AMA-1/MSP1 fusion protein" are used interchangeably, and both mean the fusion protein comprising the amino acid sequence of *Plasmodium* Merozoite Surface Protein 1, and the amino acid sequence of *Plasmodium* merozoite Apical Membrane Antigen-1, between which there may or may not be hinge sequence. In addition, the fusion protein of merozoite Apical Membrane Antigen-1 and Merozoite Surface Protein 1 may or may not contain a signal peptide, and may or may not contain an initial methionine.

As used herein, the term "*Plasmodium* merozoite Apical Membrane Antigen-1 (AMA-1) amino acid sequence" refers to a part of the amino acid sequence of the fusion protein of the present invention. The sequence basically has the same amino acid sequence with natural sequence and segment thereof, and basically has the same antigen activity with natural *Plasmodium* AMA1. A preferred *Plasmodium* AMA-1 amino acid sequence comprises (but is not limited to): the amino acid sequence of natural AMA-1, the amino acid sequence of the whole ectodomain of AMA-1, the amino acid sequence of domain III of AMA-1, the amino acid sequence of domain I-III of AMA-1, and the amino acid sequence with glycosylation sites eliminated.

As used herein, the term "Merozoite Surface Protein 1 (MSP1) amino acid sequence" refers to a part of the amino acid sequence in the fusion protein. This sequence basically has the same amino acid sequence with natural MSP1 sequence of *Plasmodium*, and basically has the same antigen activity with natural MSP1. A preferred *Plasmodium* MSP1 amino acid sequence comprises (but is not limited to): the amino acid sequence of natural MSP1, the amino acid sequence of MSP1 19 KD C-terminal, and the amino acid sequence with glycosylation sites eliminated.

The amino acid sequences of AMA-1 and MSP1 and analogues thereof could be obtained from different *Plasmodium* such as human *Plasmodium* (for example, *Plasmodium falciparum, Plasmodium vivax, Plasmodium malariae,* and *Plasmodium ovale*), and animal *Plasmodium* (such as mouse *Plasmodium*, monkey *Plasmodium*, etc.).

There is no limitation on the linking mode or order between the AMA-1 amino acid sequence and the MSP1 amino acid sequence. E.g, it can be head-tail linking, head-head linking or tail-tail linking.

As used herein, the term "hinge" refers to a short peptide between the AMA-1 amino acid sequence and the MSP1 amino acid sequence used in linking them. There is no special limitation on the length of the hinge. It may even be 0 when the AMA-1 amino acid sequence directly link with the MSP1 amino acid sequence. Usually, the hinge will not significantly affect the formation of correct folding and special conformation of the AMA-1 amino acid sequence and the MSP1 amino acid sequence. Some examples of the hinge include (but is not limited to):

Preferably, the hinge has the following amino acid sequence:

(a) An amino acid sequence containing 3–15 amino acids made of hydrophobic amino acids Gly and Pro. For example Gly-Pro-Gly-Pro-Gly-Pro (SEQ ID NO: 7);

(b) An amino acid sequence encoded by Multiple Cloning Sites. This sequence usually contains 5–20 amino acids, and preferably 10–20 amino acids. The example comprises (but is not limited to): TGLQPTRGIDDITSPVD (SEQ ID NO: 8);

(c) A *Plasmodium* antigen amino acid sequence except AMA-1 and MSP1, such as *Plasmodium* Circumsporozoit Protein, TRAP, and 175KD Erythrocytic Binding Protein, etc.

(d) A combined amino acid sequence of (a), (b) and/or (c). One example of the hinge made by (a) and (b) is GPGPGT-GLQPTRGIDDITSPVDGPGPGP (SEQ ID NO: 9).

In addition, an amino acid sequence that does not affect the immunogenicity of AMA-1 and MSP1 could be added to the N-terminal or C-terminal of the AMA-1/MSP1 fusion protein. Preferably, these added amino acid sequences could help expression (such as a signal peptide), purification (such as 6His tag, alpha-factor signal peptide cleavage site (Glu-Lys-Arg) in *Saccharomyces cerevisiae*), or could enhance the immunogenicity of an AMA-1/MSP1 fusion protein (for example, the sequence of cytokine, such as interferon and IL, etc.).

The total DNA sequence encoding the fusion protein of the present invention could be artificially synthesized. The encoding DNA sequence of AMA-1 and/or MSP1 could also be obtained through PCR amplification or synthesis, and then be ligated together to form the DNA sequence encoding the fusion protein of the present invention.

To increase the expression yield in host cells, alterations could be made to the encoding sequence of the AMA-1/MSP1 fusion protein, for example, using the codons preferred by the host cells, or eliminating the sequence adverse to gene transcription and translation. In one example of the present invention, the codons preferred by yeast were adopted, and the sequence in the gene adverse to gene transcription and translation, comprising intron cleavage site, transcription termination sequence, etc. were eliminated. ScaI, HindIII and KpnI unique cleavage sites were incorporated at nucleotide base 494, 1085 and 1621 respectively of this gene to facilitate gene synthesis and cloning.

After obtaining the DNA sequence encoding the fusion protein of the present invention, it was incorporated into proper expression vector, and then transferred to proper host cells. Finally, the transformed host cells were cultured, and the fusion protein of the present invention was obtained through expression and purification processes.

As used herein, the term "vector" includes a plasmid, a cosmid, an expression vector, a cloning vector and a virus vector, etc.

In the present invention, various vectors known in the art such as commercially available vectors could be used. For example, a commercially available vector can be operably linked to the nucleic acid sequence encoding the new fusion protein in the present invention under an expression regulatory sequence, and thus forms the expression vector.

As used herein, the term "operably linked" refers to such a condition where a certain part of a linear DNA sequence could affect the activity of another certain part in the same linear DNA sequence. For example, if a signal peptide plays a role in the secretion of polypeptides, then the DNA sequence encoding the signal peptide (precursor sequence of secretion) is operably linked to the DNA of the polypeptide; if a promoter controls the transcription of a sequence, then it is operably linked to the encoding sequence. If a ribosomal binding site is located at a position which can initiate translation, then it is operably linked to the encoding sequence. Generally, "operably linked" means adjacency, while in the precursor sequence of secretion it means adjacency in reading frame.

As used herein, the term "host cell" comprises prokaryotic cells and eukaryotic cells. The commonly used prokaryotic host cells comprise *E. coli, Bacillus subtilis*, etc. The commonly used eukaryotic cells comprise yeast cells, insect cells, mammal cells, etc. Preferably, the host cells are eukaryotic cells, more preferably yeast cells.

After obtaining the transformed host cells, the host cells could be cultured under proper conditions to express the fusion protein of the present invention. Then the expressed fusion protein is isolated.

In another aspect, the present invention further comprises the specific antibody against the AMA-1/MSP1 fusion protein, particularly the monoclonal antibody. "Specific" herein means that the antibody can bind to the AMA-1/MSP1 fusion protein or its segment. Preferably, the term refers to those antibodies that can bind to the AMA-1/MSP1 fusion protein or its segment but do not recognize and bind to other non-relative antigen molecules. The present invention further comprises those antibodies that can bind to the AMA-1/MSP1 fusion protein in modified or unmodified forms.

The present invention comprises not only an intact monoclonal or polyclonal antibody, but also an antibody segment with immune activity, such as Fab' or (Fab)$_2$ segment; a heavy chain of antibody; a light chain of antibody; a single chain Fv molecule reconstructed by genetic engineering; or a chimeric antibody.

The antibodies of the present invention can be prepared through various techniques well known by persons skilled in the art. For example, the purified AMA-1/MSP1 fusion protein or the segment with immunogenicity thereof can be administrated to an animal to induce the generation of a polyclonal antibody. Similarly, cells that express the AMA- 1/MSP1 fusion protein or the segment with immunogenicity thereof can be used to immunize an animal for the generation of antibody. The monoclonal antibody of the present invention can be prepared through the hybridoma technique (see Kohler et al., Nature 256: 495, 1975; Kohler et al., Eur. J. Immunol. 6: 511,1976; Kohler et al., Eur. J. Immunol. 6: 292, 1976; Hammerling et al., In Monoclonal Antibodies and T Cell Hybridomas, Elsevier, N.Y., 1981).

The production of polyclonal antibody can be achieved by using the AMA-1/MSP1 fusion protein or polypeptide to immunize animals such as rabbit, mouse, rat, etc. Various adjuvants can be used to increase immune reaction, which comprise, but are not limited to, Freund's adjuvant.

In another aspect of the invention, a vaccine containing the fusion protein of the present invention is provided. The vaccines of the present invention are mainly prophylactic (i.e. to prevent from infection).

These vaccines include an immune antigen or an immunogen, an immunogenic polypeptide, protein or protein segment, or a nucleic acid (such as RNA or DNA), and are usually combined with a "pharmaceutically acceptable carrier" which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the vaccine composition of the present invention could further contain other immunogenic *Plasmodium* proteins, such as *Plasmodium* circumsporozoite Protein and an immunogenic segment or a fusion protein thereof.

Preferred adjuvants to enhance effectiveness of the composition include, but are not limited to: (1) aluminum salts (alum), such as aluminum hydroxide, aluminum phosphate, aluminum sulfate, etc., (2) ISA 720 adjuvant, and (3) Freund's adjuvant, etc.

The vaccine composition (comprising an antigen, a pharmaceutically acceptable carrier and/or an adjuvant), usually comprises a diluent, such as water, saline, glycerol, ethanol, etc. Additionally, auxiliary substances, such as wetting or emulsifying agents, pH buffering substances, and the like, may be present in such vehicles. Furthermore, the vaccine composition, including immunogenic composition, may contain the antigen, polypeptide, protein, and protein segment or nucleotide acid together with pharmaceutically acceptable vehicles.

More specifically, vaccines comprising immunogenic compositions comprise an immunologically effective amount of the immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g., nonhuman primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

Typically, the vaccine compositions or immunogenic compositions are prepared as injectables, either as liquid solutions or emulsions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

The immunogenic compositions are conventionally administered parenterally, e.g., by injection, either subcutaneously or intramuscularly. Additional formulations suitable for other modes of administration include oral formulations, suppositories, and transdermal applications. Dosage treatment may be a single dose schedule or a multiple dose schedule. The vaccine may be administered in conjunction with other immunoregulatory agents.

A model of vaccine is DNA vaccine, i.e. the vaccine that contains the DNA sequence encoding the fusion protein of the present invention.

The advantages of the present invention lie in:

(1) In the AMA-1/MSP1 fusion protein, after fusion of the AMA-1 and MSP1-19 into one molecule, the conformations thereof are very close to their respective natural conformations, with at least 6 monoclonal antibody epitopes being identical to that of the natural proteins.

(2) The expression product of the AMA-1/MSP1 fusion protein could be secreted into the protein-free culture supernatant, which will be convenient for isolation and purification. The purity could achieve higher than 98%.

(3) The expression level of the AMA-1/MSP1 fusion protein is high. Particularly, the expression level of PfCP-2 is extremely high. The expression yield in a shaking flask is 840 mg/L, while the expression yield in a 15-L ferment pot could achieve 2,600 mg/L.

(4) The AMA-1/MSP1 fusion protein is very high immunogenic. The ELISA antibody titer thereof is more than 4 million, and this antibodies also contain AMA-1 and MSP1 specific antibodies.

(5) The immune serum against the AMA-1/MSP1 fusion protein has very strong inhibition upon in vitro growth of the parasite. This immune serum could inhibit more than 98% of the parasite growth in vitro after being diluted 6.7 times.

The invention is further illustrated by the following examples. These examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLE 1

Synthesis of PfCP-1 and PfCP-2

1. Design of the Fusion Antigen

The amino acid sequence of the fusion protein derived from extodomain of AMA-1 and MSP1-19 of *Plasmodium falciparum* 3D7 line. A hinge sequence comprising hydrophobic amino acid Gly-Pro was inserted into the two antigens to avoid the interaction of the antigens and retain their native conformation. In addition, 8 restriction sites were inserted between the two antigens, which allowed further insertion of other antigens. The XhoI site and *Saccharomyces cerevisiae* alpha-factor signal peptide cleavage sequence were introduced to the N-terminus of the fusion protein. Three potential glycosylation sites were eliminated by substituting Ala for Asn. The fusion antigen PfCP-1 comprised 660 amino acids while PfCP-2 260 amino acids. The schematic diagram of the two antigens and N- and C-terminal sequence of the antigens were shown in FIG. 1.

2. Design of the Synthetic Gene

The amino acid sequence of PfCP-1 was reverse-translated into DNA sequence using codon usage optimized for expression in yeast. The designed sequence was examined and modified to exclude sequences which might cause problem during synthesis, cloning and expression of the gene. They included putative splice donor, acceptor sites and terminator sequences, etc. The unique restriction sites ScaI, HindIII and KpnI were introduced for gene synthesis and cloning at position 494, 1085 and 1621, respectively (FIG. 2). The entire synthetic PfCP-1 gene comprised 1997 bp while PfCP-2 797 bp.

3. Synthesis of the Fusion Antigen Gene

Construction of PfCP-1 Gene

The sequences of the gene containing 1997 bp were divided into four fragments named PfCP-1a, PfCP-1b, PfCP-1c and PfCP-1d, respectively. There was an overlapping region between two adjacent fragments and a unique restriction site was designed to ligate the fragments (FIG. 2A, indicated by arrow). Thus, unique restriction sites Sca I, Hind III and Kpn I were introduced at position 494, 1085 and 1621 bp.

The 512 bp PfCP-1a fragment was synthesized with 8 oligonucleotides using PCR-based synthesis method. The PCR reaction was performed by denaturation at 95° C. for 10 sec, annealing at 55° C. for 30 sec and elongation at 72° C. for 90 sec with 30 cycles. The PCR products were analyzed on the 1% agarose gel and purified using Qiagen DNA gel purification Kit. The gene fragment and vector pBluescript were digested with XhoI and EcoRI. In 20 ul reaction system, 2 ug DNA was digested at 37° C. for 1 hr with 5 units of enzyme XhoI and EcoRI, respectively. The digested gene fragment and vector were ligated to generate a recombinant plasmid. E. coli DH5α was transformed with the recombinant plasmid. Amp+ transformants were selected for isolation of plasmid containing the target gene. DNA sequencing of target gene was carried out and the results showed that one of three clones had error-free. Similar strategy was used to assemble the rest fragments, i.e. PfCP-1b, PfCP-1c and PfCP-1d. The fragments were recovered using appropriate restriction enzymes XhoI/ScaI, ScaI/HindIII HindIII/KpnI and KpnI/EcoRI and ligated into the vector digested by XhoI/EcoRI, thereby forming gene PfCP-1 which encoded a fusion protein having amino acid sequence of SEQ ID NO:1.

E. coli strain DH5α was transformed with the recombinant plasmid containing the entire gene. The synthetic gene is stable in E. coli because no error on the gene recovered from the bacteria after several passages was observed.

To express the PfCP-1 gene in Pichia pastoris, the DNA sequence encoding Lys-Arg sites was introduced to the 5'-terminus of the gene to recreate the alpha-factor signal peptide cleavage sites. To facilitate purification, 6× his tag was added to the 5'-terminus of the gene to generate a PfCP-1$^{+his}$ while PfCP-1$^{-his}$ had no tag. Unique site XhoI and EcoRI were introduced at the 5'-terminal and 3'-terminal of the gene, respectively to facilitate the cloning of the gene into expression plasmid.

Construction of PfCP-2 Gene

To construct PfCP-2 gene, a pair of primers were synthesized. The 5' primer: 5'-ccg ctc gag aaa aga caa caa tca tct tac att g-3' (SEQ ID NO: 4) was corresponding to postion 1234 of PfCP-1 gene. The 3' primer: 5'-cg gaa ttc cta tta atg atg atg atg atg att aga gga aga gca gaa g-3' (SEQ ID NO: 5) hybridized to the C-terminal sequence. Using the two primers, we amplified the 797 bp PfCP-2 gene encoding amino acid sequence of SEQ ID NO:2 using PfCP-1 as template DNA which encodes the protein containing 6× his tag.

The PfCP-2 gene encoding amino acid sequence of SEQ ID NO: 3 without 6His tag was generated using another 3' primer 5'-cg gaa ttc cta tta att aga gga aga gca gaa g-3' (SEQ ID NO: 6).

EXAMPLE 2

Expression of PfCP in Pichia pastoris 2.1 Construction of Expression Vector

PfCP-1 or PfCP-2 was cloned in yeast expression vector pPIC9 using XhoI and EcoRI sites. The Saccharomyces cerevisiae alpha-factor signal peptide and its cleavage site (Lys-Arg) was introduced in frame with the PfCP coding sequences. Thus the mature secretary proteins should not contain any signal peptide residue.

Figure 5:
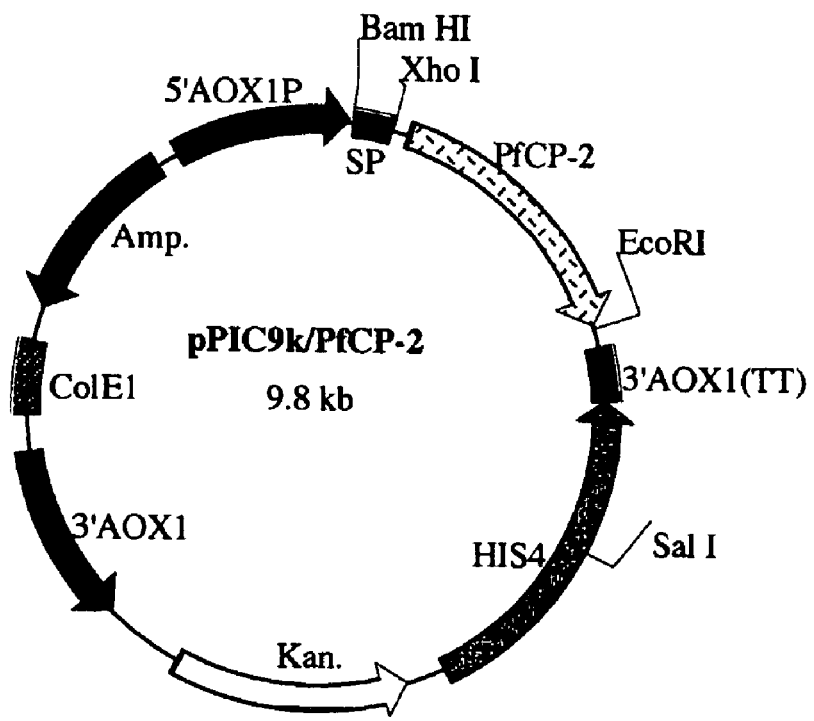
FIG. 5: the schematic diagram for the pPIC9k/PfCP-2 recombinant expression plasmid.

The vector pPIC9K was identical to pPIC9 except for the presence of the Kanamycin resistance gene to screen for multiple-copy insertion. Using the BamHI and SalI sites on the vectors, transferring the BamHI/SalI fragments from pPIC9 to pPIC9k to generate pPIC9K/PfCP-1 (FIG. 4) and pPIC9K/PfCP-2 vectors (FIG. 5).

2.2 Transformation of Pichia pastoris SMD1168

The pPIC9K/PfCP-1 and pPIC9K/PfCP-2 was linearized with SalI. Transformation of Pichia pastoris strain SMD1168 was carried out by electroporation with 10 ug of linearized DNA. The His+ transformants were further screened for transformation with multiple-copy insertion on YPD plates containing various concentration of G418. The insertion of target gene need to be confirmed by PCR using genomic DNA isolated from the His+/G418 positive clones. The clones confirmed by PCR were used for expression.

The Pichia pastoris strain expressing PfCP-1 was deposited at the China Center for Type Culture Collection (CCTCC) on Nov. 22, 2000 with the accesion number of CCTCC NO:M 200026.

2.3 Expression

The transformants were grown in MGY medium containing glycerol for 24 hrs. The cells were harvested and the pellet was resuspended in BMMY medium containing methanol to induce expression. The supernatant as well as cell pellet were analyzed for protein expression by coomassie strained SDS-PAGE gel every 24 hr. The result showed that after methanol induction, a PfCP-2 band appeared at 32 kD. The expression product significantly increased with the elongation of time (FIG. 7). Specific monoclonal antibody mAb5.2 was used to detect the product and the result showed that the dimmer and tetramer of PfCP-2 was detected besides the 32 kD protein (FIG. 7B). In addition, the doublet of PfCP-2 protein was observed on the SDS-PAGE gel. N-terminal sequence analysis of the product showed that the doublet had different N-terminus, with 9 amino acid deletion in the band with low molecular weight. Expression of PfCP-1 protein was detectable with a band at 72 kD by Western blot but very week band appeared on SDS-PAGE and Coomassie stained gel (FIG. 6).

EXAMPLE 3

Interaction of the AMA-1/MSP-1 Fusion Protein and a Panel of Monoclonal Antibodies MSP1-19 and AMA-1 are cysteine-rich proteins that form several disulfide bonds. Moreover, their functional antibodies are disulfide bond-dependent. Thus the key issue for this invention is to retain all conformational epitopes after fusion of the two proteins into one molecule. Therefore, to gain an insight into conformational properties of the fusion proteins, in this experiment a panel of monoclonal antibodies were used to react with PfCP-1 and PfCP-2 fusion protein.

Total 13 monoclonal antibodies, of them 10 recognizing conformational epitopes, were used to interact with PfCP-1. The expression products were subjected to electrophoresis in SDS-PAGE under non-reducing conditions, and then transferred onto pyroxylin membrane. The membrane-bound proteins were reacted with each of the 13 mAbs respectively and visualized via the AP-conjugate secondary antibody following standard procedures. The results showed that all 13 specific mAbs interacted with the expression protein (Table 1).

TABLE 1

Interaction of PfCP-1 with a panel of monoclonal antibodies

| Antigen | Specificity | mAb No. | Epitope type | Interaction region | Western blot PfCP-1 from P. pastoris |
|---|---|---|---|---|---|
| MSP-1 | Conserved | 5.2 | conformational | MSP 1–19 | + |
| | | 12.8 | conformational | MSP 1–42 | + |
| | | 12.10 | conformational | MSP 1–19 | + |
| | | 2.2 | conformational | MSP 1–19 | + |
| | | 6.1 | conformational | MSP 1–42 | + |
| | | 1E1 | conformational | MSP 1–19 | + |
| | | 2F10 | conformational | MSP 1–19 | + |
| | | 8A12 | conformational | MSP 1–19 | + |
| | | 111.4 | conformational | MSP 1–19 | + |
| | | 111.2 | conformational | MSP 1–19 | + |
| AMA-1 | 3D7 | 1F9 | | AMA-1 | + |
| | | 2C5 | | AMA-1 | + |
| | | 5G8 | | AMA-1 | + |

Six conformational monoclonal antibodies were used to react with PfCP-2 protein under reducing and non-reducing conditions. 6% β-mercaptoethanol was added to the sample to reduce the protein. Same amount of reduced and non-reduced protein was loaded on each lane of SDS-PAGE gel and was detected with the antibodies according to the procedures described above. The results showed that all the monoclonal antibodies interacted with PfCP-2 in reduction-sensitive manner (FIG. 8).

Conclusion: The fusion protein resembles closely to native conformation after fusing of AMA-1 and MSP1-19 into one molecule. At least the six epitopes recognized by the antibodies are identical to the native ones.

EXAMPLE 4

Fermentation and Purification of AMA-1/MSP 1 Fusion Protein

Expression conditions were optimized to achieve the yield of 840 mg/L in flask expression.

During fermentation of the yeast strain in 15-liter fermentor, the cells grow fast and increase by index exponent. The cell density could reach $OD_{660}=112.5$ value. During the period of methanol induction, the cell density was maintained at the same level while the target protein appeared in the first 3–7 hours and then dramatically increased. By 53 hours after induction, the expression yield reached 2600 mg/L.

PfCP-2 expression product was purified by two steps. At the first step protein was purified with Ni-NTA column because 6His residues located at the C-terminus of PfCP-2 that can combine to the Ni-NTA chelate. The bound proteins were eluted by a buffer containing 250 mM imidazole. At the second step, proteins eluted from Ni-NTA were further purified by gel filtration chromatography. The protein of >98% purity was obtained by the two-step purification (FIG. 9).

EXAMPLE 5

Immunizing Rabbit with PfCP-2

Figure 10:
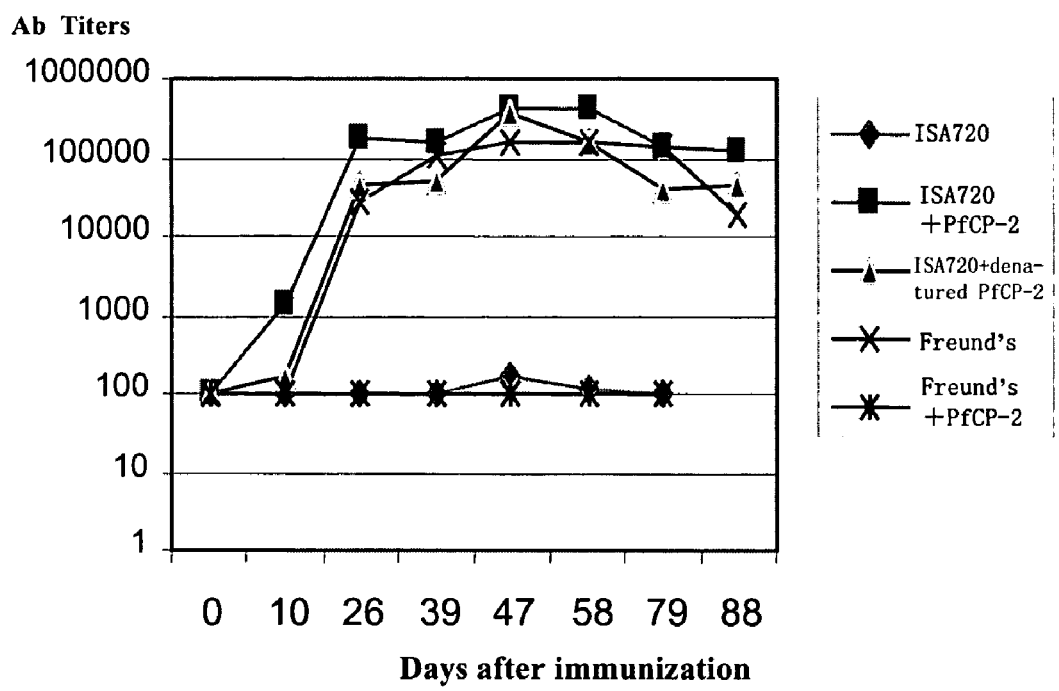
FIG. 10: the PfCP-2 specific IgG level of the immunized rabbit serum measured by ELISA. Each group respectively is: ISA720 adjuvant+PfCP-2; ISA720 adjuvant+denatured PfCP-2; Freund's adjuvant; and Freund's adjuvant+PfCP-2.
Figure 11:
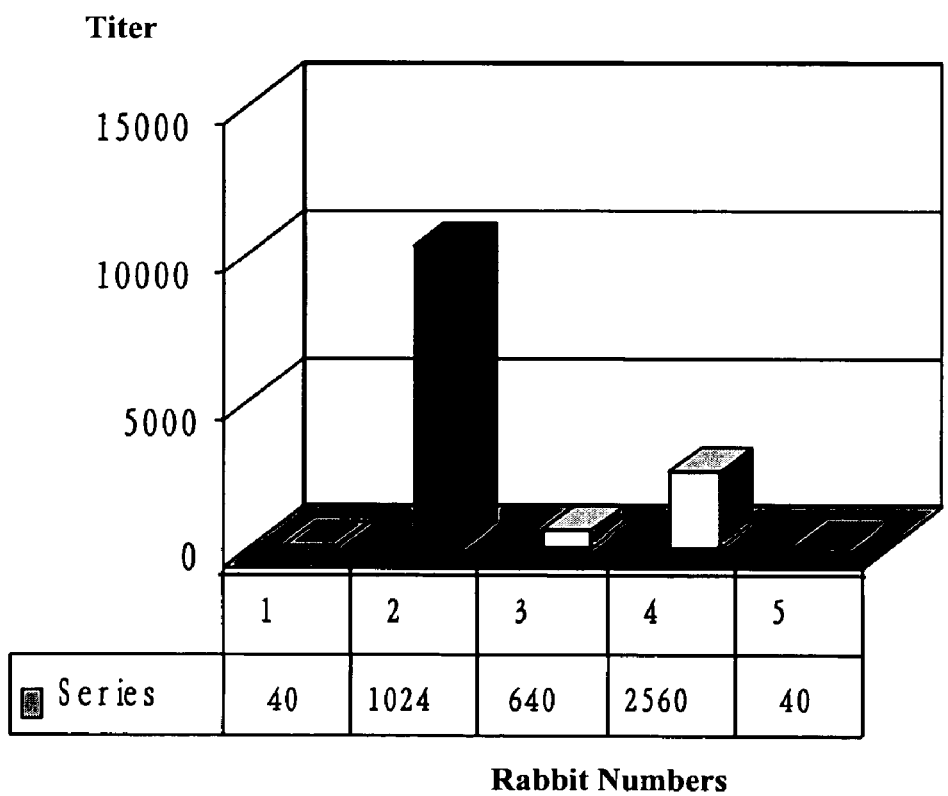
FIG. 11: the PfCP-2 specific IgG level of the immunized rabbit serum measured by IFA. Each group respectively is: ISA720 adjuvant+PfCP-2; ISA720 adjuvant+denatured PfCP-2; Freund's adjuvant; and Freund's adjuvant+PfCP-2.

In this experiment, rabbits were immunized with the purified PfCP-2 protein formulated with either Freund's adjuvant or Montanide ISA 720 adjuvant, respectively. The animals were divided into 5 groups. The groups 1–5 were ISA 720, ISA 720+PfCP-2, ISA 720+denatured PfCP-2, Freund's+PfCP-2 and Freund's adjuvant, respectively. The rabbits were immunized four times on Day 0, 12, 28 and 42, respectively. Before and 7 days after each immunization, sera was prepared by bleeding. Specific antibodies were analyzed. Methods involving this experiment was described as the following:

PfCP-2 antigen was formulated with Freund's adjuvant at ratio 1:1 while with ISA 720 adjuvant at 3:7 (v/v). The denatured PfCP-2 antigen was prepared as following: the antigen solution was mixed with solid urea to final concentration of 8M and incubated at 50° C. for 60 min. DTT was added to a final concentration of 20 mM and incubated at 50° C. for 6 hr. Sodium iodoacetate was added to a final concentration of 60 mM and mixture was incubated at room temperature (RT) for 60 minutes. The protein solution was dialysed in 0.1M boric acid buffer overnight (100 mM boric acid, 137 mM NaCl, PH 7.5). The rabbits were inoculated intromuscularly four times at 0, 12, 28 and 42 days. The protein dose was 800, 400, 400 and 200 ug, respectively. The animals were bleeded on Day 10, 26, 39 and 47 and sera were analyzed for specific antibodies by ELISA and IFA. (FIGS. 10,11)

The protocol for ELISA: 96-well microtiter plates were coated with 0.1 ug of PfCP-2 or P. flaciparum (Pf) parasites proteins. 100 ul diluted sera were added to each well and incubated for 1 h at 37° C. Every sample was repeated in three wells. After washing, enzyme-label secondary antibodies was added to each well. The incubation and washing were carried out as described above. TMD was used as substrate. The plates were read at an absorbance of 450 nm. Cutoff values were determined as the mean plus three standard deviations for the pre-immunization sera.

The ELISA results showed that no specific antibodies was induced in both adjuvant control groups, but significant specific antibodies was induced in the other three immunized groups. P. flaciparum parasites obtained from in vitro cultivation were used as antigens for IFA. Groups 2 and 4 had higher level of specific antibodies with IFA titer of 1:10240 and 1:2560 respectively while the group of denatured protein (Group 3) had much lower level of the antibodies with titer only 1:640. As expected, sera from the two control groups had not antibodies recognizing the parasite (<1:40) (FIG. 11). The sera of rabbits immunized with PfCP-2 was further tested by ELISA for specific IgG against the individual components of the fusion protein, AMA-1 and MSP1-19. The antigens used for this testing included the AMA-1 that was produced in E. coli and refolded as well as MSP 1-19 that was expressed in yeast. It was demonstrated that rabbit sera interacted with the individual components of AMA-1 and MSP 1-19 specifically (FIG. 12).

EXAMPLE 6

In Vitro Growth Inhibition Assay

FCC1/HN line of P. flaciparum was cultured in vitro using Trager's Candle Jar method. The inhibition assay was performed by using this method. The inhibition rate was calculated according to the following formula:

$$\text{Inhibit rate}(IR) = \frac{\text{parasitaemia in control group} - \text{parasitaemia in experimental group}}{\text{parasitaemia in control group}} \times 100\%$$

Method: P. flaciparum FCC1/HN line was cultured in vitro as described by Trager and Jansen. The culture medium was refreshed every 24 hrs and fresh red blood cells were added to culture every four day. To prepare synchronous parasites for the inhibition assay, the infected erythrocytes were mixed with 5% sorbitol and incubated at RT for 30 minutes. The treated parasite was further cultured at 30° C. for 24 hours. Thus most parasites developed into schizonts. The initial culture was prepared to have 2% haematocrit and 0.5% parasitaemia. 200 ul of the culture was added to each well containing different concentration of test sera. After 24 or 72 hours, thin smears were made and stained with Giemsa's solution to determine parasitaemia under the microscope.

Preparation of anit-sera: The rabbit blood was taken by cardiac puncture and put into sterile tubes to wait for coagulation. The anti-sera were collected from coagulation by centrifugation. sera was heat-inactivated at 56° C. 30 min and sterilized by filtration before using for inhibition assays.

Deletion of IgG from immune sera: The IgG in immune sera was eliminated by Protein A column according to the manufactory instruction. This step was repeated until no IgG was observed in the flowthrough detected by SDS-PAGE. Moreover, bounded IgG was eluted from the column.

The results of in vitro inhibition assay showed that immune sera from rabbits immunized with PfCP-2 antigen formulated either with Freund's adjuvant or ISA 720 adjuvant inhibited the growth of more than 98% parasites after diluted at 6.7 times. The inhibition was dependent on presence of the specific antibodies and the conformation of PfCP-2. (FIGS. 13–16)

Result:

(1) The immune sera obtained from rabbits immunized with PfCP-2 formulated with Freund's adjuvant inhibited 96.3% parasite growth while sera from Freund's adjuvant control had no significant effect on parasite growth. (IR: 6.41%) (FIG. 13)

Figure 14:
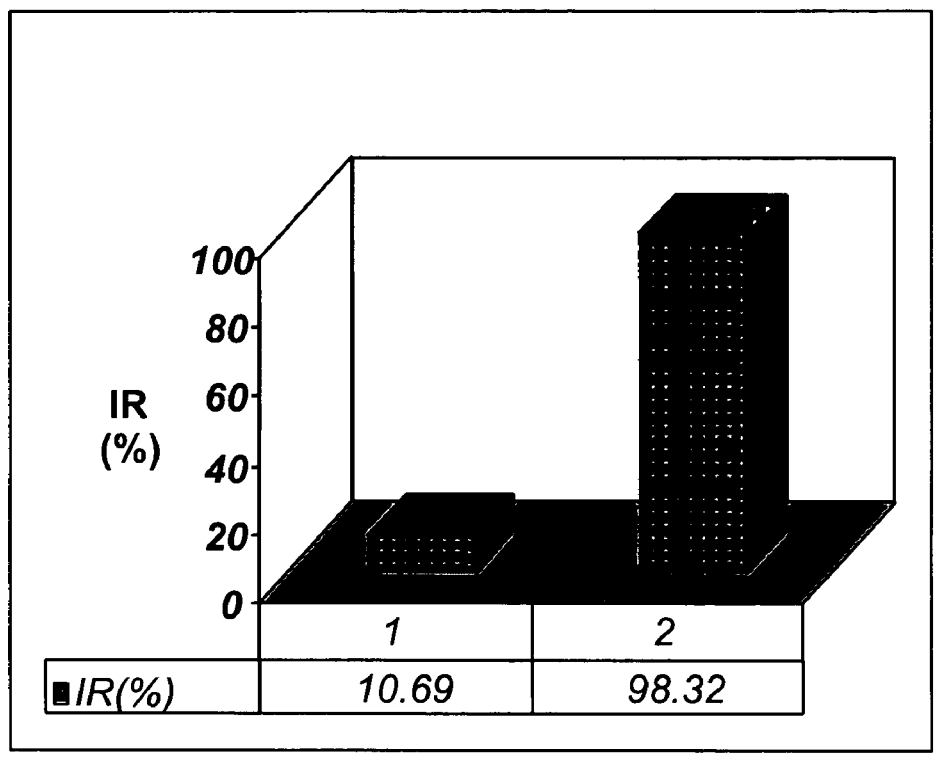
FIG. 14: the in vitro inhibition of the parasite growth by immune sera(2). Each group is: 1. ISA720 adjuvant; and 2. ISA720 adjuvant+PfCP-2.

(2) The immune sera obtained from rabbits immunized with PfCP-2 formulated with ISA720 adjuvant inhibited 98.32% parasite growth while sera from ISA720 adjuvant control had no significant effect on parasite growth. (IR: 0.69%) (FIG. 14)

Figure 15:
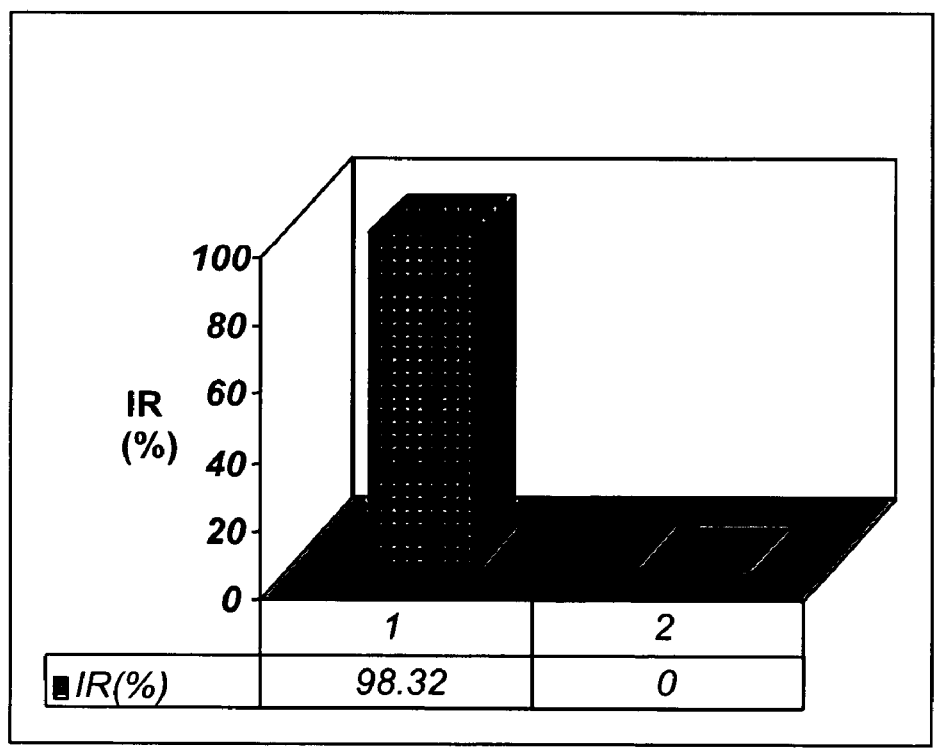
FIG. 15: the in vitro inhibition of the parasite growth by immune sera(3). Each group is: 1. ISA720 adjuvant+PfCP-2; and 2. ISA720 adjuvant+denatured PfCP-2.

(3) The immune sera obtained from rabbits immunized with denatured PfCP-2 protein by DTT as well as 8M urea and alkylated, formulated with ISA 720 adjuvant did not inhibit parasite growth at all. (IR: 0%) (FIG. 15)

Figure 16:
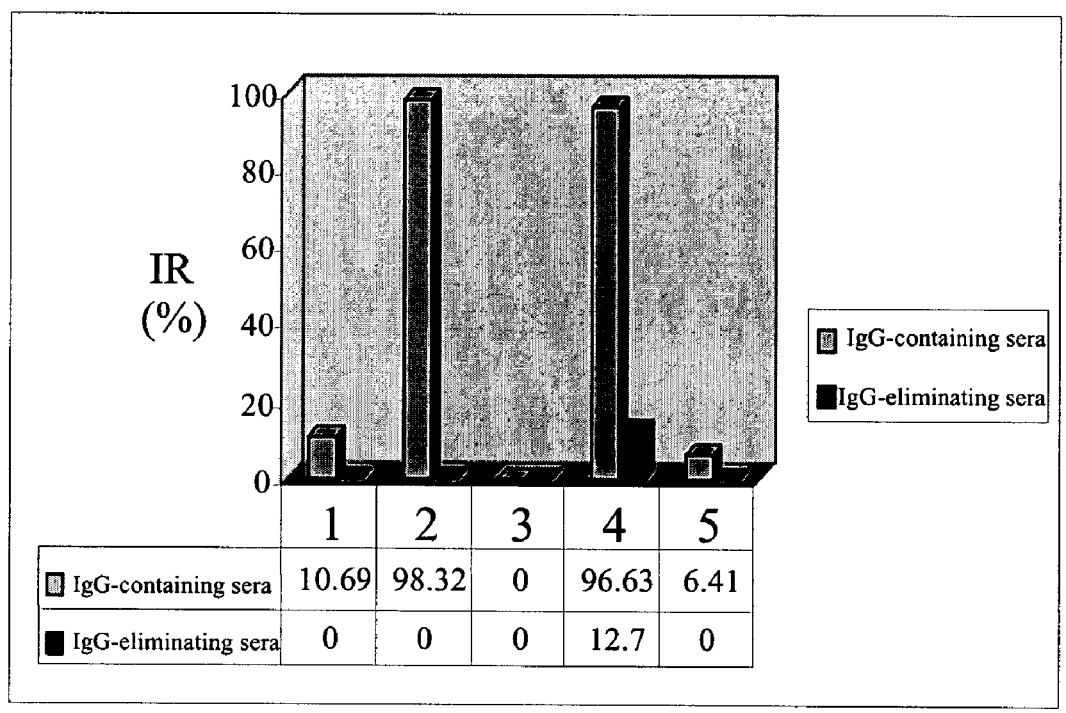
FIG. 16: the in vitro inhibition of the parasite growth by immune sera(4). Each group is: 1. ISA720 adjuvant; 2. ISA720 adjuvant+PfCP-2; 3. ISA720 adjuvant+denatured PfCP-2; 4. Freund's adjuvant+PfCP-2; and 5. Freund's adjuvant.

(4) Immune sera removed of all IgG by protein A column was tested for inhibition of parasite growth in vitro. The result showed that IgG-eliminating sera from rabbits immunized with the antigen formulated with both ISA720 and Freund's adjuvant had no effective on the parasite growth with inhibition rates of 0% and 12.7%, respectively (FIG. 16).

The study on the Growth Inhibition Assay indicated: (1) The immune sera induced by PfCP-2 almost completely inhibited the parasite growth in vitro(IR: >98%) when diluted at 6.7 times and the inhibition was dependent on presence of IgG basing on the fact that the sera removed of total IgG was not shown to inhibit parasite growth. (2) Although Freund's adjuvant is a powerful adjuvant, it can be used only in animals. However, ISA 720 adjuvant (produced by French SEPPIC Co.) has been used in clinical trials. Our results showed that the antibody level induced with ISA 720 was comparable to that with Freund's adjuvant. Thus, ISA720 adjuvant could be an appropriate adjuvant for PfCP-2 vaccine candidate in human use. (3) Induction of inhibitory antibodies to PfCP-2 were dependent on its conformation because the denatured agent did not induce any inhibitory antibodies. Therefore, it is essential to produce PfCP-2 recombinant protein resembling closely to its native conformation.

EXAMPLE 7

Pfcp-2 Combined Vaccine

In this example, the combined vaccine of Pfcsp-2 and other Plasmodium circumsporozoite protein or its immunogenetic fragment were prepared. $Pfcsp^{RC}$ was specifically used which had a part of the sequence of Plamodium falciparum circumsporozoite protein, comprising 15 NANP repeating sequences and the whole C-terminus sequence. The whole gene of $Pfcsp^{RC}$ was synthesized by using the codon preferred for Pichia Hansen, highly secreted and expressed in Pichia Hansen, and was isolated and purified to get $Pfcsp^{RC}$.

The immunity produced by Pfcsp-2 is directed against early phase Plasmodium, and the immunity produced by $Pfcsp^{RC}$ is directed against late phase Plasmodium.

The result of co-immunization of rabbit with purified $Pfcsp^{RC}$ and Pfcp-2 showed that, after 4 tims immunization, the antibody titer of the group immunized with Pfcp-2 alone was 1/1,604,000, and the antibody titer of the group immunized with $Pfcs^{RC}$ was 1/136,000. However, the co-immunized group produced antibodies directed at both antigens with remarkable increase in titers. The antibody titer against Pfcp-2 and $Pfcsp^{RC}$ were 1/2,859,000 and 1/443,000, respectively. This result suggests that the combined immunization of two antigens can not only produce antibodies against Plasmodium in different phases, but also improve the immunogenicity of the two antigens.

| coating antigen | blood collecting time | \multicolumn{3}{c}{The antibody assay for rabbits combination immunized with Pfcp-2 and Pfcsp$^{RC}$ (×10$^4$)} |
|---|---|---|---|---|
| | | Pfcp-2 | Pfcsp$^{RC}$ | Pfcp-2+Pfcso$^{RC}$ |
| Pfcp-2 | after 2$^{nd}$ immunization | 39.52 | — | 36.02 |
| | after 3$^{rd}$ immunization | 108.60 | — | 107.74 |
| | after 4$^{th}$ immunization | 164.40 | — | 285.90 |
| Pfcsp$^{RC}$ | after 2$^{nd}$ immunization | — | 4.41 | 5.35 |
| | after 3$^{rd}$ immunization | — | 4.41 | 9.56 |
| | after 4$^{th}$ immunization | — | 13.60 | 44.30 | note:
1. The values in the table were geometrical means for 3 rabbits.
2. Dose of immunization: The dose of Pfcp-2 and Pfcsp$^{RC}$ alone were 200 μg, respectively. The dose of combination immunized group is 200 μg Pfcp-2 and 200 μg Pfcsp$^{RC}$.
3. The adjuvant used in the immunization experiment is ISA720, i.m.
4. The values in the table were antibody titers assayed by ELISA.

All the documents cited herein are incorporated into the invention as reference, as if each of them is individually incorporated. Further, it would be appreciated that, in the above teaching of invention, the skilled in the art could make certain changes or modifications to the invention, and these equivalents would still be within the scope of the invention defined by the appended claims of the application.

SEQUENCE LISTING

```
<160> NUMBER OF SEQ ID NOS: 9

<210> SEQ ID NO 1
<211> LENGTH: 654
<212> TYPE: PRT
<213> ORGANISM: artificial sequence
<220> FEATURE:
<221> NAME/KEY: misc_feature
<222> LOCATION: (1)..(654)
<223> OTHER INFORMATION: fusion protein of AMA-1 and MSP1

<400> SEQUENCE: 1

Leu Glu Lys Arg Glu Ala Glu Ala Gln Asn Tyr Trp Glu His Pro Tyr
1               5                   10                  15

Gln Asn Ser Asp Val Tyr Arg Pro Ile Asn Glu His Arg Glu His Pro
            20                  25                  30

Lys Glu Tyr Glu Tyr Pro Leu His Gln Glu His Thr Tyr Gln Gln Glu
        35                  40                  45

Asp Ser Gly Glu Asp Glu Asn Thr Leu Gln His Ala Tyr Pro Ile Asp
    50                  55                  60

His Glu Gly Ala Glu Pro Ala Pro Gln Glu Gln Asn Leu Phe Ser Ser
65                  70                  75                  80

Ile Glu Ile Val Glu Arg Ser Asn Tyr Met Gly Asn Pro Trp Thr Glu
                85                  90                  95

Tyr Met Ala Lys Tyr Asp Ile Glu Glu Val His Gly Ser Gly Ile Arg
            100                 105                 110

Val Asp Leu Gly Glu Asp Ala Glu Val Ala Gly Thr Gln Tyr Arg Leu
        115                 120                 125

Pro Ser Gly Lys Cys Pro Val Phe Gly Lys Gly Ile Ile Ile Glu Asn
    130                 135                 140

Ser Gln Thr Thr Phe Leu Thr Pro Val Ala Thr Gly Asn Gln Tyr Leu
145                 150                 155                 160

Lys Asp Gly Gly Phe Ala Phe Pro Pro Thr Glu Pro Leu Met Ser Pro
                165                 170                 175
```

-continued

```
Met Thr Leu Asp Glu Met Arg His Phe Tyr Lys Asp Asn Lys Tyr Val
            180                 185                 190
Lys Asn Leu Asp Glu Leu Thr Leu Cys Ser Arg His Ala Gly Asn Met
        195                 200                 205
Ile Pro Asp Asn Asp Lys Asn Ser Asn Tyr Lys Tyr Pro Ala Val Tyr
    210                 215                 220
Asp Asp Lys Asp Lys Lys Cys His Ile Leu Tyr Ile Ala Ala Gln Glu
225                 230                 235                 240
Asn Asn Gly Pro Arg Tyr Cys Asn Lys Asp Glu Ser Lys Arg Asn Ser
                245                 250                 255
Met Phe Cys Phe Arg Pro Ala Lys Asp Ile Ser Phe Gln Gln Tyr Thr
            260                 265                 270
Tyr Leu Ser Lys Asn Val Val Asp Asn Trp Glu Lys Val Cys Pro Arg
        275                 280                 285
Lys Asn Leu Gln Asn Ala Lys Phe Gly Leu Trp Val Asp Gly Asn Cys
    290                 295                 300
Glu Asp Ile Pro His Val Asn Glu Phe Pro Ala Ile Asp Leu Phe Glu
305                 310                 315                 320
Cys Asn Lys Leu Val Phe Glu Leu Ser Ala Ser Asp Gln Pro Lys Gln
                325                 330                 335
Tyr Glu Gln His Leu Thr Asp Tyr Glu Lys Ile Lys Glu Gly Phe Lys
            340                 345                 350
Asn Lys Gln Ala Ser Met Ile Lys Ser Ala Phe Leu Pro Thr Gly Ala
        355                 360                 365
Phe Lys Ala Asp Arg Tyr Lys Ser His Gly Lys Gly Tyr Asn Trp Gly
    370                 375                 380
Asn Tyr Asn Thr Glu Thr Gln Lys Cys Glu Ile Phe Asn Val Lys Pro
385                 390                 395                 400
Thr Cys Leu Ile Gln Gln Ser Ser Tyr Ile Ala Thr Thr Ala Leu Ser
                405                 410                 415
His Pro Ile Glu Val Glu Asn Asn Phe Pro Cys Ser Leu Tyr Lys Asp
            420                 425                 430
Glu Ile Met Lys Glu Ile Glu Arg Glu Ser Lys Arg Ile Lys Leu Asn
        435                 440                 445
Asp Asn Asp Glu Gly Asn Lys Lys Ile Ile Ala Pro Arg Ile Phe
    450                 455                 460
Ile Ser Asp Asp Lys Asp Ser Leu Lys Cys Pro Cys Asp Pro Glu Met
465                 470                 475                 480
Val Ser Gln Ser Thr Cys Arg Phe Phe Val Cys Lys Cys Val Glu Arg
                485                 490                 495
Arg Ala Glu Val Thr Ser Asn Asn Glu Val Val Lys Glu Glu Tyr
            500                 505                 510
Lys Asp Glu Tyr Ala Asp Ile Pro Glu His Lys Pro Thr Tyr Asp Lys
        515                 520                 525
Met Gly Pro Gly Pro Gly Thr Gly Leu Gln Pro Thr Arg Gly Ile Asp
    530                 535                 540
Asp Ile Thr Ser Pro Val Asp Gly Pro Gly Pro Leu Gln Ile
545                 550                 555                 560
Ser Gln His Gln Cys Val Lys Lys Gln Cys Pro Gln Asn Ser Gly Cys
                565                 570                 575
Phe Arg His Leu Asp Glu Arg Glu Glu Cys Lys Cys Leu Leu Asn Tyr
            580                 585                 590
```

```
Lys Gln Glu Gly Asp Lys Cys Val Glu Asn Pro Gln Pro Thr Cys Asn
            595                 600                 605

Glu Asn Asn Gly Gly Cys Asp Ala Asp Ala Lys Cys Thr Glu Glu Asp
        610                 615                 620

Ser Gly Ser Asn Gly Lys Lys Ile Thr Cys Glu Cys Thr Lys Pro Asp
625                 630                 635                 640

Ser Tyr Pro Leu Phe Asp Gly Ile Phe Cys Ser Ser Ser Asn
            645                 650

<210> SEQ ID NO 2
<211> LENGTH: 260
<212> TYPE: PRT
<213> ORGANISM: artificial sequence
<220> FEATURE:
<221> NAME/KEY: misc_feature
<222> LOCATION: (1)..(260)
<223> OTHER INFORMATION: fusion protein of AMA-1 and MSP1

<400> SEQUENCE: 2

Leu Glu Lys Arg Gln Gln Ser Ser Tyr Ile Ala Thr Thr Ala Leu Ser
1               5                   10                  15

His Pro Ile Glu Val Glu Asn Asn Phe Pro Cys Ser Leu Tyr Lys Asp
            20                  25                  30

Glu Ile Met Lys Glu Ile Glu Arg Glu Ser Lys Arg Ile Lys Leu Asn
        35                  40                  45

Asp Asn Asp Asp Glu Gly Asn Lys Lys Ile Ile Ala Pro Arg Ile Phe
    50                  55                  60

Ile Ser Asp Asp Lys Asp Ser Leu Lys Cys Pro Cys Asp Pro Glu Met
65                  70                  75                  80

Val Ser Gln Ser Thr Cys Arg Phe Phe Val Cys Lys Cys Val Glu Arg
                85                  90                  95

Arg Ala Glu Val Thr Ser Asn Asn Glu Val Val Val Lys Glu Glu Tyr
            100                 105                 110

Lys Asp Glu Tyr Ala Asp Ile Pro Glu His Lys Pro Thr Tyr Asp Lys
        115                 120                 125

Met Gly Pro Gly Pro Gly Thr Gly Leu Gln Pro Thr Arg Gly Ile Asp
    130                 135                 140

Asp Ile Thr Ser Pro Val Asp Gly Pro Gly Pro Gly Pro Leu Gln Ile
145                 150                 155                 160

Ser Gln His Gln Cys Val Lys Lys Gln Cys Pro Gln Asn Ser Gly Cys
                165                 170                 175

Phe Arg His Leu Asp Glu Arg Glu Glu Cys Lys Cys Leu Leu Asn Tyr
            180                 185                 190

Lys Gln Glu Gly Asp Lys Cys Val Glu Asn Pro Gln Pro Thr Cys Asn
        195                 200                 205

Glu Asn Asn Gly Gly Cys Asp Ala Asp Ala Lys Cys Thr Glu Glu Asp
    210                 215                 220

Ser Gly Ser Asn Gly Lys Lys Ile Thr Cys Glu Cys Thr Lys Pro Asp
225                 230                 235                 240

Ser Tyr Pro Leu Phe Asp Gly Ile Phe Cys Ser Ser Ser Asn His His
                245                 250                 255

His His His
        260

<210> SEQ ID NO 3
<211> LENGTH: 254
<212> TYPE: PRT
```

<213> ORGANISM: artificial sequence
<220> FEATURE:
<221> NAME/KEY: misc_feature
<222> LOCATION: (1)..(254)
<223> OTHER INFORMATION: fusion protein of AMA-1 and MSP1

<400> SEQUENCE: 3

```
Leu Glu Lys Arg Gln Gln Ser Ser Tyr Ile Ala Thr Thr Ala Leu Ser
1               5                  10                  15

His Pro Ile Glu Val Glu Asn Asn Phe Pro Cys Ser Leu Tyr Lys Asp
            20                  25                  30

Glu Ile Met Lys Glu Ile Glu Arg Glu Ser Lys Arg Ile Lys Leu Asn
        35                  40                  45

Asp Asn Asp Asp Glu Gly Asn Lys Lys Ile Ile Ala Pro Arg Ile Phe
    50                  55                  60

Ile Ser Asp Asp Lys Asp Ser Leu Lys Cys Pro Cys Asp Pro Glu Met
65                  70                  75                  80

Val Ser Gln Ser Thr Cys Arg Phe Phe Val Cys Lys Cys Val Glu Arg
                85                  90                  95

Arg Ala Glu Val Thr Ser Asn Asn Glu Val Val Lys Glu Glu Tyr
            100                 105                 110

L

-continued

<400> SEQUENCE: 5
cggaattcct attaatgatg atgatgatga tgattagagg aagagcagaa g          51

<210> SEQ ID NO 6
<211> LENGTH: 33
<212> TYPE: DNA
<213> ORGANISM: artificial sequence
<220> FEATURE:
<221> NAME/KEY: misc_feature
<222> LOCATION: (1)..(33)
<223> OTHER INFORMATION: primer

<400> SEQUENCE: 6
cggaattcct attaattaga ggaagagcag aag          33

<210> SEQ ID NO 7
<211> LENGTH: 6
<212> TYPE: PRT
<213> ORGANISM: artificial sequence
<220> FEATURE:
<221> NAME/KEY: misc_feature
<222> LOCATION: (1)..(6)
<223> OTHER INFORMATION: linker

<400> SEQUENCE: 7

Gly Pro Gly Pro Gly Pro
1               5

<210> SEQ ID NO 8
<211> LENGTH: 17
<212> TYPE: PRT
<213> ORGANISM: artificial sequence
<220> FEATURE:
<221> NAME/KEY: misc_feature
<222> LOCATION: (1)..(17)
<223> OTHER INFORMATION: linker

<400> SEQUENCE: 8

Thr Gly Leu Gln Pro Thr Arg Gly Ile Asp Asp Ile Thr Ser Pro Val
1               5                   10                  15

Asp

<210> SEQ ID NO 9
<211> LENGTH: 28
<212> TYPE: PRT
<213> ORGANISM: artificial sequence
<220> FEATURE:
<221> NAME/KEY: misc_feature
<222> LOCATION: (1)..(28)
<223> OTHER INFORMATION: linker

<400> SEQUENCE: 9

Gly Pro Gly Pro Gly Thr Gly Leu Gln Pro Thr Arg Gly Ile Asp Asp
1               5                   10                  15

Ile Thr Ser Pro Val Asp Gly Pro Gly Pro
            20                  25

What is claimed is:

1. A fusion protein comprising:
   an amino acid sequence of *Plasmodium* apical membrane antigen-1 (AMA-1), an amino acid sequence of *Plasmodium* merozoite surface protein 1 (MSP1), and a hinge between the amino acid sequence of the apical membrane antigen-1 and the amino acid sequence of the merozoite surface protein 1,
   wherein the amino acid sequence of AMA-1 is selected from the group consisting of the amino acid sequence of natural full-length AMA-1, the amino acid sequence of the whole ectodomain of AMA-1, the amino acid sequence of domain III of AMA-1, and the amino acid sequence of domain I-III of AMA-1; and
   the amino acid sequence of MSP1 is selected from the group consisting of the amino acid sequence of natural full-length MSP1 and the amino acid sequence of MSP1 19KD C-terminal;
   the hinge comprising an amino acid sequence selected from the group consisting of:
   (a) an amino acid sequence containing 6 amino acids comprising hydrophobic amino acids Gly and Pro;
   (b) an amino acid sequence encoded by multiple cloning sites; and
   (c) a combination of (a) and (b).

2. The fusion protein according to claim 1 wherein the hinge contains:
   an amino acid sequence containing 6 amino acids made of hydrophobic amino acids Gly and Pro.

3. The fusion protein according to claim 1 comprising an amino acid sequence set forth in SEQ ID NO: 1, 2 or 3.

4. An isolated DNA molecule encoding the fusion protein of claim 1.

5. A vector comprising the DNA molecule of claim 4.

6. A host cell comprising the vector of claim 5.

7. The host cell according to claim 6, wherein the cell is a yeast *Pichia pastoris* deposited in CCTCC under accession Number of CCTCC NO: M200026.

8. A method of preparing the fusion protein of claim 1 comprising the steps of:
   growing the host cell of claim 6 under a condition appropriate for the expression, thereby expressing the fusion protein, and
   isolating the fusion protein.

9. A method for producing a polyclonal antibody, which inhibits the growth of *P. falciparum* in vitro, comprising the following steps:
   (i) administering the fusion protein of claim 1 to an animal, thereby inducing the generation of a polyclonal antibody; and
   (ii) isolating the polyclonal antibody.

10. The method of claim 9 wherein the fusion protein comprises an amino acid sequence set forth in SEQ ID NO: 1, 2 or 3.

* * * * *